United States Patent
Koczab

(10) Patent No.: US 6,452,062 B1
(45) Date of Patent: *Sep. 17, 2002

(54) COMPOSITE NONWOVEN MATERIAL AND ITS APPLICATION TO ANY ABSORBENT ARTICLE OF HYGIENE

(75) Inventor: Jean-Pierre Koczab, Bondues (FR)

(73) Assignee: SCA Hygiene Products AB, Gothenberg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,931

(22) Filed: Dec. 19, 1997

Related U.S. Application Data

(62) Division of application No. 08/553,299, filed as application No. PCT/FR94/00607 on May 24, 1994, now Pat. No. 5,820,615.

(30) Foreign Application Priority Data

May 26, 1993 (FR) .............................. 93 06327

(51) Int. Cl.⁷ .......................... A61F 13/15; B32B 5/08; B32B 5/26; D04H 1/48
(52) U.S. Cl. ...................... 604/383; 604/378; 604/384; 442/388; 442/381; 442/392; 442/361; 442/334; 442/402; 442/409
(58) Field of Search ................... 442/334, 361, 442/381, 388, 392, 402, 403, 409, 407; 604/378, 383, 384, 367, 370, 366

(56) References Cited

U.S. PATENT DOCUMENTS

| | | | |
|---|---|---|---|
| 3,206,351 A | | 9/1965 | Smith, II |
| 3,545,442 A | | 12/1970 | Wicker et al. .............. 128/296 |
| 3,772,107 A | | 11/1973 | Gentile et al. ............. 156/62.8 |
| 3,936,555 A | | 2/1976 | Smith, II ..................... 428/151 |
| 3,940,532 A | * | 2/1976 | Smith, II ..................... 428/218 |
| 3,956,560 A | | 5/1976 | Smith, II ..................... 428/218 |
| 4,275,105 A | | 6/1981 | Boyd et al. .................. 428/128 |
| 4,285,342 A | | 8/1981 | Mesek ......................... 128/287 |
| 4,307,721 A | * | 12/1981 | Tsuchiya et al. ............ 128/290 |
| 4,377,615 A | * | 3/1983 | Suzuki et al. ............... 156/176 |
| 4,537,822 A | * | 8/1985 | Nanri et al. ................. 428/212 |
| 4,652,484 A | | 3/1987 | Shiba et al. ................. 428/286 |
| 4,726,987 A | * | 2/1988 | Trask et al. ................. 428/282 |
| 4,830,915 A | * | 5/1989 | Diaz-Kotti .................. 428/110 |
| 4,883,707 A | * | 11/1989 | Newkirk ..................... 428/219 |
| 5,178,932 A | * | 1/1993 | Perkins et al. .............. 428/198 |
| 5,257,982 A | * | 11/1993 | Cohen et al. ................ 604/378 |
| 5,296,290 A | * | 3/1994 | Brassington ................. 428/300 |
| 5,470,326 A | * | 11/1995 | Dabi et al. .................. 604/358 |
| 5,556,392 A | * | 9/1996 | Koczab ....................... 442/388 |
| 5,611,879 A | * | 3/1997 | Morman ...................... 156/201 |
| 5,629,005 A | * | 5/1997 | Brassington et al. ....... 424/402 |
| 5,669,798 A | * | 9/1997 | Koczab ....................... 156/291 |
| 5,820,615 A | * | 10/1998 | Koczab ....................... 156/264 |
| 5,843,064 A | * | 12/1998 | Koczab ....................... 604/378 |
| 5,873,963 A | * | 2/1999 | Trombetta et al. .......... 156/148 |
| 5,879,344 A | * | 3/1999 | Koczab ....................... 442/402 |
| 6,087,551 A | * | 7/2000 | Pereira ........................ 604/358 |
| 6,103,953 A | * | 8/2000 | Cree et al. ................... 604/365 |
| 6,168,849 B1 | * | 1/2001 | Braverman et al. ......... 156/148 |

FOREIGN PATENT DOCUMENTS

| | | |
|---|---|---|
| DE | 3029315 | 2/1981 |
| EP | 252041 A3 | 1/1988 |

\* cited by examiner

*Primary Examiner*—Cheryl A. Juska
(74) *Attorney, Agent, or Firm*—Burns, Doane, Swecker & Mathis, L.L.P.

(57) ABSTRACT

Composite nonwoven material through which liquid can pass at a high speed and having an excellent resistance to rewetting and fluffing. The material comprises at least one first layer (2) of combed-type fibres and a second layer (3) of combed-type fibres, the fibres of the first layer having a denier greater than that of the fibres of the second layer, the layers being joined to one another by needling. Application to absorbent sanitary articles.

8 Claims, 1 Drawing Sheet

COMPOSITE NONWOVEN MATERIAL AND ITS APPLICATION TO ANY ABSORBENT ARTICLE OF HYGIENE

This application is a divisional, of Application Ser. No. 08/553,299, filed Nov. 22, 1995 now U.S. Pat. No. 5,820,615 which is a 371 of PCT/FR94/00607 filed May 24, 1994.

BACKGROUND OF THE INVENTION

The invention relates generally to a new nonwoven material which, when employed as surface voile or sheet or as a supplement to the surface voile as strip in the crotch region in an absorbent article of hygiene such as a diaper or dressing for the incontinent, allows better isolation of the user's skin from the absorbent part of the article of hygiene. In particular, this new material is favorable to the time taken by the body fluids to pass through and to resistance to rewetting, and does not become fluffy.

In general, absorbent articles of hygiene, such as diapers and dressings for the incontinent, comprise an outer layer of liquid-impervious material, a pad made of absorbent material and a surface voile or sheet which is permeable to body fluids such as urine, of size and shave which are similar to those of the impervious outer layer of the article. The purpose of this surface voile which is permeable to body fluids is to isolate the skin from the moistened absorbent pad. Consequently, the surface voile must have an appropriate degree of softness and provide the required isolation between the skin and the absorbent pad. The purpose of the absorbent pad is to absorb the fluids and consequently it must have a high rate of absorption and a high absorbency. A particularly effective absorbent pad is described in document EP-A-0,232,729. This absorbent pad or mat is made up of a sheet of long absorbent fibers, the faces of said sheet being lined with a layer of cellulose wadding. The sheet lined with the layers of wadding is needled from both sides.

In the absorbent articles of hygiene absorbent mats or pads are covered by a surface voile or by a strip in the crotch region, generally made of nonwoven material, the purpose of which is to isolate the skin from the absorbent pad and which must provide a pleasant contact with the skin and the required isolation from the absorbent pad. These surface voiles or sheets and strips in the crotch region must exhibit, as essential properties, a pleasant contact with the skin, a high rate of permeation by, the body fluids, a good resistance to rewetting and must not become fluffy.

Document FR-A-2,588,285 describes a multilayer nonwoven textile which has at least two layers of nonwoven voile, one of the layers being made up of fibers of bilobar cross-section and the other layer being made up of fibers of trilobar cross-section. Each voile layer is preferably obtained by the technique of bonding when spinning (spun-bonded) and the two voile layers are joined together to form the multilayer nonwoven by heat-bonding in the compacted and noncontinuous regions.

Document WO 87/07117 describes an absorbent article of hygiene comprising an absorbent body surrounded by a cover. This surface cover or voile consists of two layers of nonwoven material. The first layer of nonwoven. material, in contact with the user's skin, consists of a thin layer of spun-bonded fibrous fabric made of a hydrophobic material and the second layer in contact with the absorbent body is a hydrophobic fibrous layer of melt-bonded fiber fabric, similar in construction to the first layer. These two surface voile layers are not bonded together in the region intended to come into contact with the user's body.

Document WO 88/05269 relates to a surface voile for a disposable absorbent article consisting of at least two layers of nonwoven material which can be identical or different and which are joined together by lines of adhesive forming an open pattern.

A new composite nonwoven material has also recently been developed, comprising at least one first layer consisting of a nonwoven (preferably spun-bonded) and, on this first layer, a sheet of fibers of carded type, the sheet of fibers of carded type being bonded to the base layer by needling.

Another recently developed composite nonwoven material comprises a first layer made of a nonwoven (preferably spun-bonded), a sheet of fibers of carded type and a second layer made of a nonwoven (preferably spun-bonded) of smaller weight per unit area than the first layer of nonwoven, the sheet of fibers of carded type being arranged between the first and the second layer of nonwoven, and the whole being bonded by needling.

These materials exhibit excellent body fluid pass-through times and an excellent resistance to rewetting. However, these materials have a pronounced tendency to becoming fluffy when employed as surface voile or crotch strip in absorbent articles of hygiene such as diapers.

OBJECTS AND SUMMARY

The objective of the present invention is therefore to provide a composite nonwoven material which, when employed as surface voile or crotch strip in an absorbent article of hygiene, has an excellent rate of crossing by body fluids, an excellent resistance to rewetting and which does not become fluffy.

Another objective of the invention is to provide a process for the manufacture of such a composite nonwoven material.

Finally, an objective of the present invention is to provide an absorbent article of hygiene comprising a surface voile or a crotch region strip made of such a composite nonwoven material.

According to the present invention a composite nonwoven material is produced, characterized in that it comprises a sheet of fibers of carded type which is permeable to body fluids, comprising at least one first layer of fibers of carded type and a second layer of fibers of carded type, the fibers of the first layer having a higher denier than the fibers of the second layer, the two layers being joined together by needling.

In a recommended embodiment of the composite nonwoven material according to the invention, at least one of the layers of fibers of carded type comprises fibers chosen from fibers with a low melting point, two-component fibers and fibers mixed with a binder such as a heat-reactivable adhesive or a powder with a low melting point, and the fibers of the layers are additionally bonded by heat-melting.

In another recommended embodiment of the invention the composite material comprises, in addition to the first and second layers of fibers of carded type, a third layer made of a conventional nonwoven, permeable to fluids, for example of the spun-bonded or melt-bonded type, of low weight per unit area, bonded to one of the layers of carded type, for example the layer of fibers of carded type of lower denier.

The invention also provides a process for the manufacture of a composite nonwoven material comprising the stages consisting in:

feeding a card, in the width direction, with first fibers and second fibers, the first fibers having a higher denier than the second fibers, to form adjacent or juxtaposed strips of fibers of carded type from the first and second fibers;

supplying the adjacent strips of fibers of carded type to a lapper-spreader device to cross the strips and form a sheet consisting of superposed strips of the first and second fibers;

supplying this sheet to a sheet-stretcher device to stretch the fibers of the strips and to orient them in the direction of travel while increasing the degree of vertical orientation of said fibers in order to obtain, at the exit of the sheet-stretcher device, a sheet of fibers comprising a first layer of the first fibers and a second layer of the second fibers; and subjecting the sheet formed to a needling from at least one of its sides.

In a recommended embodiment of the process according to the invention at least one of the layers of the sheet comprises fibers chosen from fibers with a low melting point, two-component fibers and fibers mixed with a binder such as a heat-reactivable adhesive or a powder of low melting point and the process additionally comprises the bonding together of the fibers of the layers by heat-melting, for example by reactivation using hot air passing through the sheet.

The process of the present invention can, additionally, comprise a supplementary stage consisting in bonding, for example by heat-melting, a third layer of a conventional nonwoven, of low weight per unit area, to one of the layers of fibers of carded type, for example to the layer of fibers of lower denier.

According to the present invention an absorbent article of hygiene is also produced, such as a diaper which comprises an outer layer made of material which is impervious to body fluids, an absorbent pad which is permeable to body fluids and on this absorbent pad either a surface voile or sheet, or a surface voile and a crotch region strip, the surface voile, when employed by itself, consisting of the composite nonwoven material according to the invention and the crotch region strip consisting of the composite nonwoven material according to the invention, and the surface voile of a preferably hydrophobic nonwoven, when a crotch region strip and a surface voile are employed together. In the article of hygiene the surface voile or the crotch region strip consisting of the composite material according to the invention is arranged so that the first layer of fibers of carded type of higher count is in direct contact with the internal surface of the absorbent pad and consequently the second layer of fibers of carded type of lower denier, or the third layer of conventional nonwoven either in direct contact with the user's skin or in contact with the outer surface of the surface voile in the case where the article comprises a surface voile made of conventional nonwoven.

In a recommended embodiment the invention provides an absorbent article of hygiene such as a diaper, which comprises an outer sheet made of material which is impervious to body fluids, an absorbent pad which is permeable to body fluids, attached to the outer layer, the outer layer and the absorbent pad comprising widened opposite end parts joined by a narrower crotch region, a surface sheet, preferably hydrophobic, a crotch region strip, permeable to body fluids, arranged between the pad and the surface sheet and similar in width to the crotch region of the pad and with a length at least equal to that of the pad, this crotch region strip consisting of the composite nonwoven material according to the invention, the first layer of fibers of carded type of higher denier being directly in contact with the inner surface of the absorbent pad when the composite material according to the invention consists solely of layers of fibers of carded type, and preferably the layer made of conventional nonwoven forming the innermost layer of the crotch region strip when the composite material according to the invention additionally comprises such a layer of conventional nonwoven.

In a particularly recommended embodiment the surface sheet comprises a median lengthwise cutout forming an opening, preferably of oblong shape, and an intermediate strip, of conventional nonwoven, similar in size to that of the crotch region strip, is arranged directly on the crotch region strip, below the surface sheet.

The crotch region strip is generally bonded to the absorbent pad by any suitable means, and in particular by adhesive bonding to the edge of the absorbent pad.

BRIEF DESCRIPTION OF THE DRAWINGS

The remainder of the description refers to the attached figures which show, respectively.

DETAILED DESCRIPTION OF THE PREFERRED EMBODIMENTS

Figure 1:
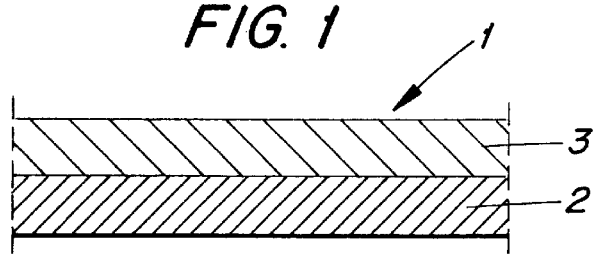
FIG. 1, a diagrammatic sectional view of a composite nonwoven material according to the invention.

With reference to FIG. 1, a composite nonwoven material 1 according to the invention has been shown diagrammatically in section. This material comprises a first layer 2 consisting of fibers of carded type and a second layer 3 also consisting of fibers of carded type. The fibers of the first layer 2 of fibers of carded type have a higher denier than the fibers of the second layer 3 of fibers of carded type. The fibers of the first layer 2 preferably have a denier of between 3 and 8 and the fibers of the second layer 3 have a count of between 1 and 3. In a particularly recommended embodiment the fibers of the first layer 2 of carded type have a denier of 4.4 whereas the fibers of the second layer 3 of carded type have a denier of 1.7.

Natural or synthetic textile fibers, such as cellulose, viscose, polyester, polyethylene, polypropylene, nylon and ethylene-propylene copolymer fibers can be employed for the layers of fibers of carded type. It is also possible to employ two-component fibers or fibers mixed with a binder such as a heat-reactivable adhesive or a polymer powder with a low melting point. The two-component fibers are fibers comprising a core made of a polymer of relatively high melting point enclosed in another polymer of relatively low melting point making it possible for the surface of the fiber to melt under moderate heating, such as heating with hot air. Such fibers are well known in the art. An example of two-component fibers is a fiber comprising a polyester core enclosed in polyolefin, for example polyethylene.

The heat-reactivable adhesives are well known in the art; an example of such an adhesive is an aqueous solution of EVA or acrylic type.

Similarly, powders with a low melting point which can be employed in the present invention are well known in the art and are generally powdered polymers with a low melting point, such as, for example a polyethylene powder.

The layers of fibers of carded type of the composite material of the invention can consist of fibers of the same kind or of different kinds, which have identical or different denier, provided that the denier of the fibers of the first layer 2 is higher than the denier of the fibers of the second layer 3.

In particular, and preferably, each of the layers consists of a mixture of fibers of little or no meltability, such as polyester fibers, with fibers with a low melting point, such as polyolefin, for example polyethylene, fibers or two-component fibers or else fibers mixed with a binder such as a heat-reactivable adhesive or powder of low melting point. The proportion of fibers of low melting point or two-component fibers or else the quantity of binder mixed with the fibers will preferably be between 5 and 30% by weight relative to the total weight.

Each of the layers may also consist of fibers of the same kind.

Similarly, the kind of the fibers may be identical or different from one layer to the next.

Of course, if the two layers consist solely of fibers with little or no meltability, such as polyester fibers, the layers in the final product are joined together solely by needling.

The layers of fibers of carded type 2, 3 may have a weight per unit area which is identical or different. The layers each preferably have a weight per unit area of between 10 and 30 g/m$^2$.

The layers of fibers of carded type 2, 3 are joined together by needling. The needling preferably has a density of between 10 and 100 needle strokes/cm$^2$ and is carried out from both sides of the composite material. This needling not only ensures a good bond between the two layers of composite material but also makes it possible to increase the vertical orientation of the fibers, thus favoring the reducing the time taken by the body fluids to pass through the composite.

When at least one of the layers of fibers of carded type is made up of fibers of low melting point, such as polyolefin fibers, for example polyethylene, of two-component fibers, or of fibers mixed with a binder, or of a mixture comprising such fibers, the bonding between the layers of fibers of carded type can also be performed by hot-melting, supplementing the above needling.

In a recommended manner, the layers are subjected to a needling operation before the reactivation with hot air for heat-melting of the fibers, because this needling improves the reactivation by the hot air passing through the fibers and their mutual immobilization, by increasing the degree of orientation of the fibers in the vertical direction.

In another embodiment (not shown) the composite material according to the invention comprises, in addition to the first and second layers of fibers of carded type, a third layer of conventional nonwoven, permeable to fluids, of low weight per unit area. This additional third layer of nonwoven may consist of any nonwoven of conventional type which is well known in the art such as, for example, a nonwoven of the spun-bonded or melt-bonded type.

The conventional nonwoven may be made of natural or synthetic textile fibers such as cellulose, viscose, polyester, polyethylene, polypropylene, nylon or ethylene-propylene copolymer fibers.

The nonwoven of conventional type preferably consists of a layer of fibers which is coated on one of its sides with a heat-reactivable adhesive or consists of a mixture of fibers comprising fibers with a low melting point, fibers mixed with a binder such as a heat-reactivable adhesive or a powder of low melting point. When the conventional nonwoven is a mixture, the proportion of fibers of a low melting point or of fibers mixed with a binder is between 5 and 30% by weight relative to the total weight. As mentioned above, this conventional nonwoven is of low weight per unit area, generally between 10 and 20 g/m$^2$, and preferably 15 g/m$^2$.

The nonwoven of conventional type is bonded by heat-melting to the second layer of fibers of carded type of lower denier, for example by running the layers of the composite on an adhesive-backing calender of the Storck type.

A process for the manufacture of the composite nonwoven material according to the invention consists in feeding a card, in the width direction, with first fibers and second fibers, the first fibers having a higher denier than the second fibers, to form adjacent or juxtaposed strips, and then from this card feeding the adjacent strips into a machine for crossing the sheets of card, called a spreader-lapper, for example a type 350 machine from the company Asselin, the purpose of which is to superpose the strips. The superposed strips are then supplied to a sheet-stretching device, for example a sheet stretcher from the company Asselin, which stretches the fibers to orient them preferentially in the direction of travel of the machine and which increases the vertical orientation of the fibers, to obtain a sheet made up of a first layer of the first fibers and a second layer of the second fibers. The sheet is next subjected to a needling operation by itself or to a needling and a reactivation by hot air through the layers of fibers to bind the fibers to each other.

The process of the invention may additionally comprise a supplementary stage in which the sheet consisting of two layers of fibers of carded type is bonded to a third layer of a conventional nonwoven, of low weight per unit area, by heat-melting this third layer of conventional nonwoven to the second layer of fibers of carded type of the sheet, that is to say the layer made of the fibers of lower denier. This heatmelting is preferably performed by running the sheet of fibers of carded type and the third layer of conventional nonwoven on an adhesive-backing calender, for example of the Storck type.

The orientation of the fibers in the composite material of carded type of the invention helps to convey the body fluids in the lengthwise direction and in the case of the manufacture of diapers with a surface voile or a crotch region strip placed in the lengthwise direction, manufactured from this composite nonwoven material, makes it possible advantageously to employ a larger proportion of the absorbent mass of the pad placed below.

This stretching of the sheet of fibers of carded type is followed by a needling which also has the effect of increasing the degree of vertical orientation of the fibers and which improves the time taken for the liquids to pass through the composite, whilst providing a good bond between the layers.

When the composite nonwoven according to the invention additionally comprises a third layer of conventional nonwoven, the resistance of the composite to fluffing is further increased.

Example of embodiment of a composite nonwoven material of carded type according to the invention.

A card is fed in the width direction with fibers comprising chiefly 4.4-denier polyester fibers and 1.7-denier polyester fibers. The fibers actually consist either of a mixture of polyester fibers and of two-component fibers comprising a polyester core and a polyethylene cover, the proportion of two-component fibers being from 5 to 30% by weight relative to the total weight, or of a mixture of polyester and polyethylene fibers of 4.4 and 1.7 deniers, the proportion of polyethylene fibers being of 5 to 30% by weight relative to the total weight.

A spreader-lapper device of 350 type from the company Asselin is fed with the juxtaposed strips originating from the card to obtain a sheet of fibers of carded type made of superposed strips of 1.7-denier fibers and 4.4-denier fibers. A sheet-stretcher from the company Asselin is fed with these superposed strips to obtain a composite sheet made of a first layer of 4.4-denier fibers and a second layer of 1.7-denier fibers. The fiber sheet is subjected to a needling which has a needling density of 20 strokes/cm$^2$ and then the sheet of fibers of carded type has a flow of hot air passed through it in order to reactivate the two-component fibers. A composite nonwoven material of carded type according to the present invention is obtained. This material has an excellent liquid passage time, good resistance to rewetting and does not become fluffy.

Furthermore when it is employed as surface voile or to complement a surface voile, as a crotch region strip, the layer of 1.7-denier fibers being placed inwards, that is to say in contact with the user's skin or with the outer surface of the surface voile, and the layer of 4.4-denier fibers directly on the absorbent pad, an absorbent article according to the invention is obtained which has a suitable softness due to the fineness of the fibers employed for the inner layer.

The composite nonwoven material obtained according to the invention also exhibits mechanical characteristics which are sufficient to be wound and employed on a conversion machine.

Figure 2:
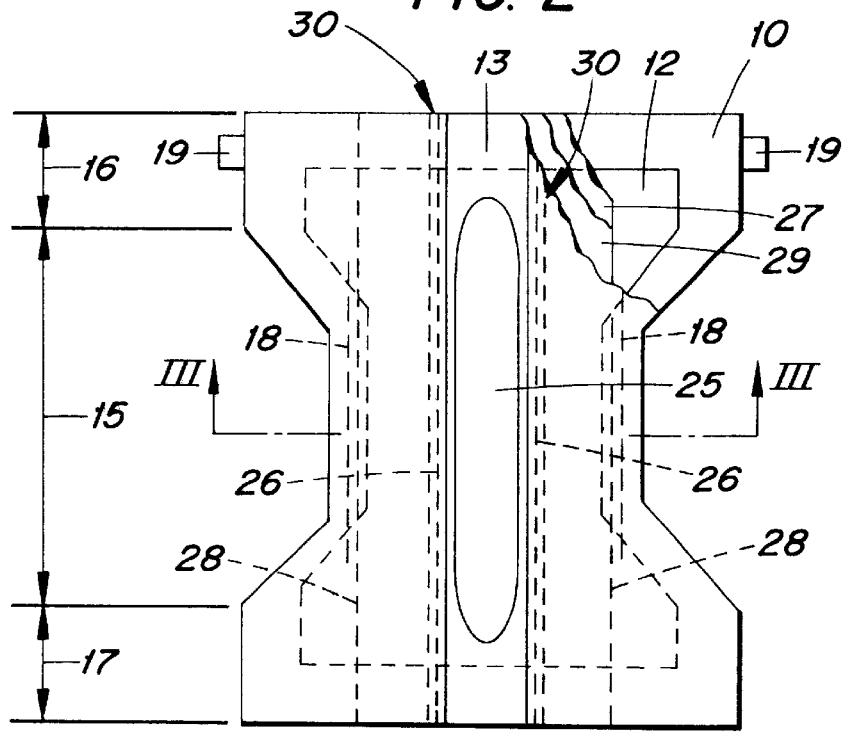
FIG. 2, a top view, with partial cutaway, of an absorbent article of hygiene such as a diaper comprising a crotch region strip consisting of the composite nonwoven material according to the invention.
Figure 3:
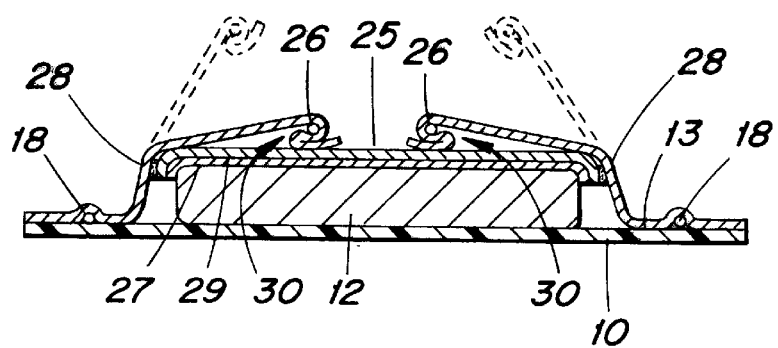
FIG. 3, a view in section along the line III—III of FIG. 2.

FIGS. 2 and 3 show, by way of example, an absorbent article of hygiene such as a diaper, comprising a crotch strip consisting of a nonwoven material of carded type according to the invention.

The diaper shown in FIGS. 2 and 3 comprises, in a manner known per se, a support sheet 10 which is impervious to liquids, an absorbent pad 12, for example of cellulose fluff pulp, optionally with incorporation of so-called superabsorbent polymeric materials, a crotch region strip 27, an intermediate strip 29 of similar size to that of the crotch region strip 27, arranged directly on this crotch region strip and generally consisting of a conventional nonwoven, and a surface sheet 13, for example a voile of hydrophobic nonwoven. The two sheets 10 and 13 are of the same size and have the same hour-glass shape, that is to say a rectangular shape with two opposite side cutouts defining, in the lengthwise direction of the diaper, a crotch region 15 of reduced width between two end regions 16 and 17 of increased width. The absorbent pad 12 arranged between the two sheets 10 and 13 is also hourglass-shaped but of smaller size than the sheets 12 and 13 which are joined to each other, for example by adhesive bonding along the whole periphery of the pad 12.

First lengthwise elastic members 18, each consisting, for example, of one or several elastic strands or yarns or of an elastic strip, are attached in the stretched state to the support sheet 10, at least in the crotch region 15 between the-back of the cutouts in the sheet 10 and the back of the corresponding cutouts in the absorbent pad 12.

Furthermore, adhesive fastenings 19 are attached to the opposite side edges in the end region 16 forming the rear part of the diaper.

The surface sheet 13 comprises, in its middle part, a middle lengthwise cutout 25 to form an opening, preferably of oblong shape. The width of the opening is markedly smaller than the width of the pad 12, preferably smaller than one half of the width of the pad 12 in the crotch region. Furthermore, the surface sheet 13 comprises, over its whole length, two Z-shaped double folds 30 in a downward direction (toward the pad 12) which are arranged on each side of the opening 25, and elastic members 26 are attached in the stretched state by adhesive bonding in the upper back-folds of these double folds 30, the two back-folds of each double fold 30 being integrally joined to one another by adhesive bonding or any other means so as to consolidate or stiffen the cover sheet 13 at this point and thus to facilitate cutting out and removing the material from the opening 25, which is made subsequently. The crotch strip 27 made of composite nonwoven material according to the invention is arranged directly above the absorbent pad over the whole length of the diaper and has a width which is at least equal to the width of the absorbent pad 12 in the crotch region. The crotch region strip 27 is bonded to the absorbent pad 12 and/or to the intermediate strip 29 by any suitable well-known means, and the intermediate strip 29, in the embodiment shown, is attached to the surface sheet 13, on the one hand on the two transverse edges of the diaper and, on the other hand, along two lengthwise lines 28, for example lines of adhesive, which are situated in a position that is slightly offset in relation to the lengthwise edges of the absorbent pad 12 in the crotch region 15.

Although the surface sheet has been shown as comprising two Z-shaped double folds 30, it is also possible to modify the -shape of these folds in any appropriate manner, for example by producing folds which are S-shaped.

Equally, the elastic members 26 can be arranged in any suitable place other than the upper back-folds, for example the lower back-folds.

The crotch strip 27 consists of a composite nonwoven material according to the invention, comprising two layers of fibers of carded type of different counts joined together by needling, the layer of fibers of carded type of the higher count being in direct contact with the absorbent pad 12.

This diaper exhibits a high rate of crossing by the liquids, good resistance to rewetting and does not become fluffy.

What is claimed is:

1. An absorbent article, comprising:

a composite nonwoven material, which is permeable to body fluids, said composite nonwoven material including a first layer of carded fibers and a second layer of carded fibers, the fiber layers each having a weight per unit area of 10 to 30 g/m$^2$, the fibers of the first layer having a higher denier than the fibers of the second layer, the first and second layers being joined together by needling with a needling density ranging from 10 to 100 needle strokes/cm$^2$ and by thermal bonding; and an absorbent core which is permeable to body fluids and attached to said composite nonwoven material, said first layer of fibers of higher denier being closest to the absorbent core.

2. The absorbent article according to claim 1, wherein the fibers of the first layer have a denier of between 3 and 8 and the fibers of the second layer have a denier of between 1 and 3.

3. The absorbent article according to claim 1, wherein the fibers of the first layer are chosen from cellulose, viscose, polyester, polyethylene, polypropylene, nylon, ethylene-propylene copolymer fibers, two-component fibers and fibers mixed with a binder that is a heat-reactivable adhesive or a powder of low melting point.

4. The absorbent article according to claim 1, wherein the first and second layers consist of polyester fibers.

5. The absorbent article according to claim 1, wherein the first and second layers consist of polyester fibers mixed with a binder that is a heat-reactivable adhesive or a powder of low melting point and the layers are additionally bonded by heat-melting.

6. The absorbent article according to claim 1, wherein at least one of the first and second layers comprises a mixture of two-component fibers and fibers mixed with a binder that is a heat-reactivable adhesive or a powder of low melting or fibers with a low melting point and the layers are additionally bonded by heat-melting.

7. The absorbent article according to claim 6, characterized in that the first and second layers comprise a mixture of two-component fibers and fibers mixed with a binder that is a heat-reactivable adhesive or a powder of low melting point or fibers with a low melting point.

8. The absorbent article according to claim 1, wherein the layers comprise mixtures of polyester fibers and of fibers chosen from two-component fibers and fibers with a low melting point, said layers being additionally bonded by heatmelting.

* * * * *